(12) United States Patent
Lee et al.

(10) Patent No.: US 6,506,886 B1
(45) Date of Patent: Jan. 14, 2003

(54) METHOD OF PREPARING FORM II CRYSTALS OF CLARITHROMYCIN

(75) Inventors: Tae-Suk Lee, Kyungki-do (KR); Ju-Cheol Lee, Seoul (KR); Kyoung-Ik Lee, Incheon (KR); Gwan-Sun Lee, Seoul (KR); Wan-Joo Kim, Seoul (KR)

(73) Assignee: Hanmi Pharm. Co., Ltd. (KR)

( * ) Notice: Subject to any disclaimer, the term of this patent is extended or adjusted under 35 U.S.C. 154(b) by 0 days.

(21) Appl. No.: 09/786,636

(22) PCT Filed: Sep. 8, 1999

(86) PCT No.: PCT/KR99/00530

§ 371 (c)(1),
(2), (4) Date: Mar. 7, 2001

(87) PCT Pub. No.: WO00/14099

PCT Pub. Date: Mar. 16, 2000

(30) Foreign Application Priority Data

Sep. 9, 1998 (KR) ............................................. 98-37181

(51) Int. Cl.$^7$ .................................................. C07M 1/00
(52) U.S. Cl. ...................................... 536/7.2; 536/18.5
(58) Field of Search .................................. 536/7.2, 18.5

(56) References Cited

U.S. PATENT DOCUMENTS 5,844,105 A * 12/1998 Liu et al. ................... 536/18.5

\* cited by examiner

Primary Examiner—Elli Peselev
(74) Attorney, Agent, or Firm—Anderson Kill & Olick, PC

(57) ABSTRACT

Form II crystals of clarithromycin can be easily prepared by treating clarithromycin of different crystal forms with water or with a mixture of water and a water-immiscible organic solvent and isolating treated crystals by filtration.

5 Claims, 1 Drawing Sheet

METHOD OF PREPARING FORM II CRYSTALS OF CLARITHROMYCIN

This application is a continuation application of International Application No. PCT/KR99/00530 filed on Sep. 8, 1999, which claims priority thereon pursuant to 35 USC section 120.

FIELD OF THE INVENTION

The present invention relates to a method of preparing Form II crystals of clarithromycin comprising treating clarithromycin with water to provide said crystals having no residual organic solvent.

BACKGROUND OF THE INVENTION

Clarithromycin, 6-O-methylerythromycin A, is a semisynthetic macrolide antibiotic of formula (I) which exhibits a wide range of antibacterial activity:

(I)

[chemical structure]

It has been discovered that clarithromycin exists in two distinct crystalline forms, "Form I" and "Form II", as described in International Publication Nos. WO 98/04573 and WO 98/04574. The crystal forms can be identified by infrared spectroscopy, differential scanning calorimetry and powder x-ray diffraction spectrophotometry. Form I crystals of clarithromycin are prepared by recrystallization from ethanol, tetrahydrofuran, isopropyl acetate, isopropyl alcohol or a mixture thereof. However, the thermodynamically more stable Form II is used in the drug formulations currently on the market.

Form II crystals of clarithromycin have been prepared by crystallization from chloroform/isopropyl ether (1:2) (see Merck Index 12th ed., pp. 395), but this method has a problem in that the resulting Form II crystals contain residual organic solvents. Alternatively, Form II crystals may be obtained by heating Form I crystals under a vacuum at 80° C. or higher for a prolonged time (see International Publication No. WO 98/04573), but this method has the problem of low productivity.

International Publication No. WO 98/04574 teaches a method of preparing clarithromycin crystal Form II using various organic solvent systems or aqueous solvents containing water-miscible organic solvents. However, this method is hampered by a relatively low yield (approximately 9 to 83%) and still has the problem of entrained organic solvents.

Accordingly, there has existed a need to develop a new simple method for preparing pure Form II crystals of clarithromycin in a high yield.

SUMMARY OF THE INVENTION

Accordingly, it is a primary object of the present invention to provide pure Form II crystals of clarithromycin having no residual solvent in a high yield.

In accordance with the present invention, there is provided a method of preparing Form II crystals of clarithromycin comprising treating clarithromycin with water or with a mixture of water and a water-immiscible organic solvent.

BRIEF DESCRIPTION OF THE DRAWINGS

The above and other objects and features of the present invention will become apparent from the following description, when taken in conjunction with the accompanying drawing wherein.

DETAILED DESCRIPTION OF THE INVENTION

Figure 1:
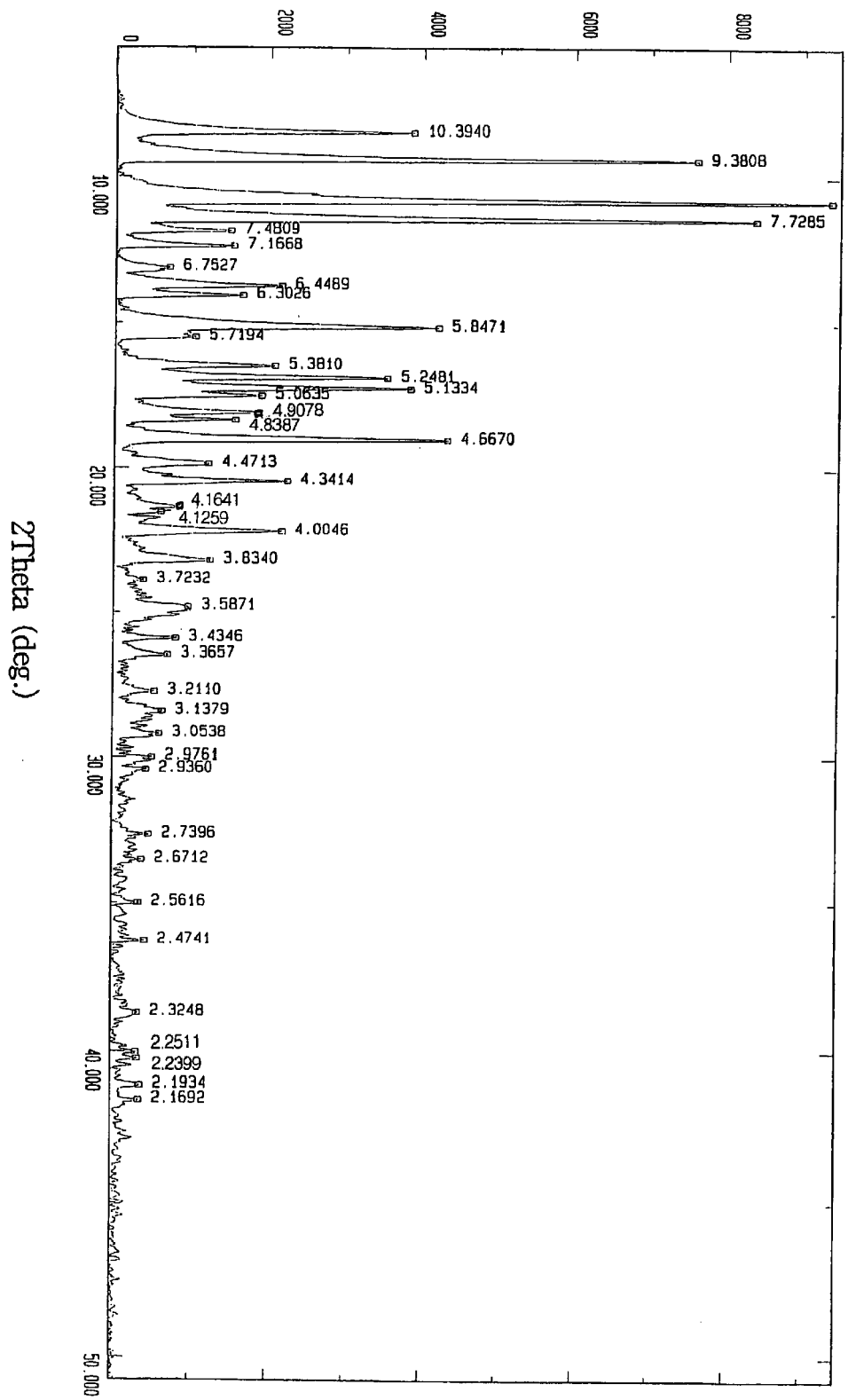
FIG. 1 shows the powder X-ray diffraction spectrum of clarithromycin crystal Form II.

The method of preparing Form II crystals of clarithromycin in accordance with the present invention comprises the step of treating clarithromycin with water or with a mixture of water and a water-immiscible organic solvent and isolating treated crystals.

The term "clarithromycin" as used herein refers to refined crystal Form I or mixtures of refined crystal Form I and Form II, or crude reaction product formed during the process of the preparation thereof. Representative methods of preparing clarithromycin are described in U.S. Pat. Nos. 4,331,803, 4,670,549, 4,672,109 and 4,990,602, and European Patent No. 260 938.

The treating step in accordance with the present invention may be performed at an ambient temperature with stirring for a period sufficient to convert Form I crystals to Form II crystals of clarithromycin, e.g., about 1 to 4 hours.

Water which may be distilled or deionized water is used in the inventive process in an amount ranging from 3 to 10 times that of clarithromycin used.

The water-immiscible organic solvents optionally used in the present invention are those which do not dissolve clarithromycin to any significant extent, and examples thereof include $C_{5-7}$ hydrocarbons, diethyl ether, ethyl acetate, methyl acetate and the like. The optional water-immiscible organic solvent functions to dissolve impurities that may be present in a clarithromycin feed, thereby further increasing the purity of the product. The organic solvent may be employed in an amount ranging from 0.5 to 2 times that of clarithromycin used.

After the clarithromycin crystals are sufficiently treated, the resultant crystals are filtered and dried in a conventional manner to give pure clarithromycin crystal Form II in a high yield of at least 95%.

The method of the present invention is very simple and provides pure Form II crystals of clarithromycin having no residual organic solvent in a high yield of greater than 95% at a low process cost.

The following Examples are intended to further illustrate the present invention without limiting its scope.

EXAMPLE 1

Recovering of Form II Crystals of Clarithromycin from Water 100 g of clarithromycin (purity: 95.5%) was added to 500 ml of water and the resulting mixture was stirred vigorously at room temperature for 2 hours. The crystals were filtered and dried overnight in a vacuum oven of 60° C. to give 97 g of clarithromycin crystal Form II (purity: 97.4%, yield: 97%).

EXAMPLE 2

Recovering of Form II Crystals of Clarithromycin from Water and Hexane 100 g of clarithromycin (purity: 95.5%) was added to 500 ml of water and the resulting mixture was stirred vigorously at room temperature for 2 hours. 100 ml of hexane was added thereto, and the mixture was further stirred at room temperature for 1 hour. The resulting crystals were filtered and dried overnight in a vacuum oven of 60° C. to give 95 g of clarithromycin crystal Form II (purity: 97.7%, yield: 95%).

EXAMPLE 3

Recovering of Form II Crystals of Clarithromycin from Water and Ethyl Acetate

The procedure of Example 2 was repeated except that ethyl acetate was used instead of hexane, to give 95 g of clarithromycin crystal Form II (purity: 98.0%, yield: 95%).

EXAMPLE 4

Recovering of Form II Crystals of Clarithromycin from Water and Methyl Acetate

The procedure of Example 2 was repeated except that methyl acetate was used instead of hexane, to give 95 g of clarithromycin crystal Form II (purity: 97.9%, yield: 95%).

EXAMPLE 5

Recovering of Form II Crystals of Clarithromycin from Water and Diethyl Ether

The procedure of Example 2 was repeated except that diethyl ether was used instead of hexane, to give 97 g of clarithromycin crystal Form II (purity: 97.5%, yield: 97%).

The powder X-ray diffraction pattern of each clarithromycin obtained in Examples 1 to 5 was identical to that of clarithromycin crystal Form II shown in FIG. 1.

While the invention has been described with respect to the above specific embodiments, it should be recognized that various modifications and changes may be made to the invention by those skilled in the art which also fall within the scope of the invention as defined by the appended claims.

What is claimed is:

1. A method of preparing Form II crystals of clarithromycin comprising treating a clarithromycin feed with a mixture of water and a water-immiscible organic solvent and isolating treated crystals by filtration.

2. The method of claim 1, wherein the water-immiscible organic solvent is selected from the group consisting of a $C_{5-7}$ hydrocarbon, diethyl ether, ethyl acetate and methyl acetate.

3. The method of claim 1 or 2, wherein the water-immiscible organic solvent is hexane.

4. The method of claim 1, wherein water is used in an amount ranging from 3 to 10 times that of the clarithromycin feed.

5. The method of claim 1, wherein the water-immiscible organic solvent is used in an amount ranging from 0.5 to 2 times that of the clarithromycin feed.

* * * * *